United States Patent
Lindsay et al.

(10) Patent No.: US 9,442,111 B2
(45) Date of Patent: Sep. 13, 2016

(54) METHOD AND APPARATUS FOR MEASURING PHOSPHORYLATION KINETICS ON LARGE ARRAYS

(71) Applicant: ARIZONA BOARD OF REGENTS, Scottsdale, AZ (US)

(72) Inventors: Stuart Lindsay, Phoenix, AZ (US); Joshua Labaer, Chandler, AZ (US)

(73) Assignee: ARIZONA BOARD OF REGENTS, Scottsdale, AZ (US)

( * ) Notice: Subject to any disclaimer, the term of this patent is extended or adjusted under 35 U.S.C. 154(b) by 0 days.

(21) Appl. No.: 14/364,953

(22) PCT Filed: Dec. 12, 2012

(86) PCT No.: PCT/US2012/069143
§ 371 (c)(1),
(2) Date: Jun. 12, 2014

(87) PCT Pub. No.: WO2013/090364
PCT Pub. Date: Jun. 20, 2013

(65) Prior Publication Data
US 2014/0357527 A1     Dec. 4, 2014

Related U.S. Application Data

(60) Provisional application No. 61/570,492, filed on Dec. 14, 2011.

(51) Int. Cl.
*G01N 27/403*     (2006.01)
*G01N 33/557*     (2006.01)
(Continued)

(52) U.S. Cl.
CPC .............. *G01N 33/557* (2013.01); *C12N 9/12* (2013.01); *G01N 33/6842* (2013.01); *G01N 2440/14* (2013.01); *G01N 2570/00* (2013.01)

(58) Field of Classification Search
CPC ... G01N 33/557; G01N 33/6842; C12N 9/12
USPC ........................................................ 257/253
See application file for complete search history.

(56) References Cited

U.S. PATENT DOCUMENTS

| | | | |
|---|---|---|---|
| 6,800,453 B2 | 10/2004 | Labaer et al. | |
| 2004/0136866 A1* | 7/2004 | Pontis | B82Y 10/00 422/400 |

(Continued)

OTHER PUBLICATIONS

Lindsay et al., (2012). "Biochemistry and semiconductor electronics—the next big hit for silicon?" J. Phys.: Condens. Matter 24(16): 164201.

(Continued)

*Primary Examiner* — Matthew Gordon
(74) *Attorney, Agent, or Firm* — McBee Moore Woodward Vanik, IP LLC.

(57) ABSTRACT

The disclosure provides for methods and apparatuses relating to technology for monitoring chemical and/or biological reactions. Some methods provided herein relate to utilization of NAPPA technology to create large protein arrays suitable for use in combination with various ISFET arrays to enable massive parallel assays of kinase activity and inhibition. Some devices provided herein relate to CMOS chips which utilize the NAPPA array technology to build protein inventories of interest upon an ISFET architecture. Further devices provided herein are capable, inter alia, of processing the arrays created by the combination of NAPPA technology and ISFET architecture.

5 Claims, 11 Drawing Sheets

(51) Int. Cl.
  *C12N 9/12* (2006.01)
  *G01N 33/68* (2006.01)

(56) References Cited

U.S. PATENT DOCUMENTS

| | | | |
|---|---|---|---|
| 2005/0089924 A1 | 4/2005 | Ho et al. | |
| 2006/0105373 A1* | 5/2006 | Pourmand | B82Y 15/00 435/6.11 |
| 2008/0071071 A1* | 3/2008 | LaBaer | G01N 33/6803 536/23.1 |
| 2010/0282617 A1* | 11/2010 | Rothberg | C12Q 1/6825 205/780.5 |
| 2010/0301398 A1 | 12/2010 | Rothberg et al. | |
| 2012/0079897 A1* | 4/2012 | Kavusi | G01N 33/48707 73/865.6 |
| 2013/0053252 A1* | 2/2013 | Xie | C12Q 1/6874 506/2 |

OTHER PUBLICATIONS

Manning et al., (2002). "The Protein Kinase Complement of the Human Genome." Science 298(5600): 1912-1934.
Lee et al., (2009). "Ion-Sensitive Field-Effect Transistor for Biological Sensing." Sensors 9: 7111-7131.
Ramachandran et al., (2004). "Self-Assembling Protein Microarrays." Science 305: 86-90.
Ramachandran et al., (2008). "Next Generation High Density Self Assembling Functional Protein Arrays." Natural Methods 5(6): 535-538.
Goncalves et al., (2008). "Detection of DNA and Proteins Using Amorphous Silicon Ion-Sensitive Thinfilm Field Effect Transistors." Biosens. Biolectron. 24: 545-551.
Nebel et al., (2006). "Alkene/Diamond Liquid/Solid Interface Characterization Using Internal Photoemission Spectroscopy." Langmuir 22(13): 5645-5653.
Estrela et al., (2005). "Field Effect Detection of Biomolecular Interactions." Electrochim. Acta. 50: 4995-5000.
Zayats et al., (2006). "Label-free and Reagentless Aptamer-Based Sensors for Small Molecules." J. Am. Chem. Soc. 128: 13666-13667.
Freeman et al., (2007). "Following a Protein Kinase Activity Using a Field-Effect Transistor Device." Chem. Commun. 33: 3450-3452.
Migita et al., (2007). "Enzyme-based field-effect transistor for adenosine triphosphate (ATP) sensing." Analytical Sciences 23(1): 45-48.
Rothberg et al., (2011). "An integrated semiconductor device enabling non-optical genome sequencing." Nature 475(7356): 348-352.

\* cited by examiner

METHOD AND APPARATUS FOR MEASURING PHOSPHORYLATION KINETICS ON LARGE ARRAYS

CROSS REFERENCE TO RELATED APPLICATIONS

This application is a §371 National Stage Application of PCT/US2012/069143, filed Dec. 12, 2012 which claims priority to U.S. Provisional Application Ser. No. 61/570,492 filed Dec. 14, 2011.

FIELD OF THE DISCLOSURE

The present disclosure is directed to methods and devices relating to detection and measurement of analytes of interest including analytes associated with protein kinase reactions.

BACKGROUND

Protein kinases are enzymes that modify neutral amino acid residues on target proteins to add a charged phosphate group. These enzymes are key regulators of cell function and the DNA encoding their expression constitutes one of the largest and most functionally diverse gene families, constituting approximately 1.7% of the entire human genome. (Manning et al., 2002).

Kinase activity represents one of the most important and prevalent signaling pathways in cells. By adding phosphate groups to substrate proteins, kinase molecules direct the activity, localization, and overall function of many proteins, and serve to orchestrate the activity of almost all cellular processes. Kinases are particularly prominent in signal transduction and co-ordination of complex cellular functions. For example, many proteins are imported into the cell nucleus once they are phosphorylated. One possibility is that they become part of an ion current flux through the nuclear pores as a result of the added charge. Once inside the nucleus, they can then act as transcription factors, regulating the expression of their target genes. By modification of substrate activity, protein kinases also control many other cellular processes, including metabolism, transcription, cell cycle progression, cytoskeletal rearrangement and cell movement, apoptosis, and differentiation. Protein phosphorylation also plays a critical role in intercellular communication during development, in physiological responses, in homeostasis, and in the functioning of the nervous and immune systems. (Manning et al., 2002).

The crucial role that kinases play in biomolecular systems makes the enzymes important targets for academic and applied research. Fundamental issues to be addressed by current biomolecular investigations include: At what rate a given kinase marks a target protein? What are the target proteins of a given kinase? How do pharmaceuticals alter and regulate kinase activity? These questions are of great scientific and economic importance, as illustrated by the fact that kinase inhibitors are one of the largest classes of drugs on the market.

There have been many developments over the past few decades that hold great promise for future kinase research. One such achievement, the sequencing of the human genome, has provided an explosion of information that is now being analyzed and studied by the scientific community. Another highly fruitful area of scientific inquiry has been the emerging field of proteomics. Researchers in the field of proteomics are applying the genetic information elucidated by the human genome project and beginning to understand the functions of encoded proteins.

This burgeoning growth in genome and proteome investigation has been ushered in by a new wave of high-throughput assays and arrays that have enabled investigators to rapidly analyze and sequence enormous amounts of genetic data. One such high-throughput assay, the DNA microarray, is able to facilitate the rapid identification and classification of thousands of genes simultaneously. A DNA microarray works by exploiting the ability of a given mRNA molecule to bind specifically to, or hybridize to, the DNA template from which it originated. By using an array containing many DNA samples, scientists can determine, in a single experiment, the expression levels of thousands of genes within a cell by measuring the amount of mRNA bound to each site on the array. With the aid of computers and computational algorithms, the amount of mRNA bound to the spots on the microarray is precisely measured, generating a profile of gene expression in the cell. (NIH Primer on Microarrays, 2011).

Another such development, the protein microarray, holds promise as a research tool that will help scientists better understand the role that the encoded proteins of the human genome play within the intact biological system. The protein microarray can be constructed by immobilizing large numbers of purified proteins and used to assay a wide range of biochemical functions.

Despite the great advances in understanding that have been brought about by this new generation of high-throughput assay technology, there are still significant technological hurdles that are inherent in the assay technology itself. For instance, DNA and protein microarray technology is normally dependent upon an optical signal being generated upon binding of an analyte of interest, i.e. detection of a fluorescently-labeled nucleic acid tag. This dependency upon a fluorescently-labeled tag brings with it consequent restraints relating to the sensitivity, speed, cost, and miniaturization capabilities of these assays. A unique technological challenge facing protein microarray technology in particular, is caused by the sensitivity and heterogeneity of proteins, which make it difficult to stably store protein arrays in a functional state for long periods of time. In contrast, DNA is a highly stable molecule capable of long-term storage. Two recent advances may help researchers overcome these previous constraints.

The first, Ion-Sensitive Field-Effect Transistor chip technology (ISFET chips) is beginning to be conceptualized as a viable method for non-optical biosensing technology that holds promise as an alternative to the traditional microarrays that are dependent upon fluorescently labeled tags. ISFET chips generally work by measuring fluctuations in ion concentration ($H^+$ or $OH^-$) in a solution that contains an analyte of interest. Therefore, large ISFET chip arrays can be constructed and the variation in charge density of an analyte of interest contained in the various wells of the chip can be measured; thereby allowing for the electronic analysis of biomolecules. (Lee et al., 2009).

The second, Nucleic Acid-Programmable Protein Array (NAPPA) technology, addresses the stability problems inherent in constructing protein arrays. NAPPA technology replaces the complex process of spotting purified proteins with the simple process of spotting plasmid DNA. NAPPA exploits the ability of researchers to transfer protein encoding regions (open reading frames; ORFs) into specialized tagged expression vectors. These new expression clones are then spotted on the array and the proteins are then produced in situ in a cell-free system and immobilized in place upon their synthesis. This minimizes direct manipulation of the proteins and produces them just-in-time for the experiment, avoiding problems with protein purification and stability. (Ramachandran et al., 2004). NAPPA arrays have been developed that allow for thousands of proteins to be produced simultaneously in situ, and with remarkably consistent protein levels displayed. (Ramachandran et al., 2008). The power of this approach is that by expressing many proteins on a single array it is possible to test the function of many proteins simultaneously.

Despite the recent advances in high-throughput assay technology, there has not been adequate utilization of these methods and devices in the study of the human proteome and in particular the human kinome. The human kinome comprises 1.7% of all human genetic information and there are over 500 proteins encoded by these genes. These kinome proteins are well known for their importance in normal cell physiology and for their role in many human diseases. Consequently, drugs related to inhibiting kinase expression are one of the largest classes available on the market. It can therefore be easily seen that an understanding of kinase activity in living systems holds great promise for addressing a whole host of human diseases and genetic conditions. Therefore, there is a need in the arena of kinase research for the implementation of new methods and devices that take advantage of the rapidly developing advances in the field of high-throughput molecular biology assays.

For the foregoing reasons, there is a need for methods and devices that can take advantage of the recent technological advances seen in the electrical biosensing arena and the advances made with protein arrays.

SUMMARY

Aspects of the present invention relate generally to methods and devices that satisfy the need in the field of kinome research for a high-throughput biosensing technology that overcomes the shortcomings inherent in optical based biosensing arrays and also addresses the shortcomings found with regard to creating stable protein microarrays. The methods and devices described herein provide a versatile new platform for proteomics, and in particular, kinome research.

Methods having the attributes of the present invention constitute a combination of ISFET technology with that of protein array technology.

In a preferred embodiment, methods of the present invention comprise a combination of ISFET technology and NAPPA technology.

Embodiments of the present invention are advantageous over previous methods utilized to study kinases. For example, there is stability in the arrays provided by utilizing NAPPA technology and there is no dependence upon optical sensors, as the phosphorylation event is detected by ISFETs. Consequently, by utilizing a preferred embodiment comprising the combination of NAPPA and ISFET technologies, one is able to realize a solution to the problems that have plagued the prior art, e.g. the inherent limitations of optical based detections systems and the instability of some protein arrays.

Devices having the attributes of the present invention also combine ISFET and protein array technology.

In a preferred embodiment, devices of the present invention comprise a combination of ISFET and NAPPA technology and therefore represent advantageous devices that are capable of being utilized to study the entire human proteome and in particular kinases.

In one embodiment, the methods of the present invention relate to evaluating phosphorylation of an array of proteins, comprising: 1) providing an array of sensors, each sensor comprising (i) one ion-sensitive field effect transistor (IS-FET), (ii) a layer of first material disposed over the sensor array and having formed therein a plurality of microwells, each microwell disposed over at least one of the ISFETs and each microwell comprising: (a) a polypeptide comprising a test amino acid sequence and an affinity tag, (b) a binding agent that recognizes the affinity tag and is attached to a surface of the microwell; 2) contacting the bound polypeptide/binding agent complex within the microwells with a second polypeptide; and 3) detecting a change in H+ or OH− ion concentration.

In another embodiment, the method of the present invention relates to evaluating phosphorylation of an array of proteins, comprising: 1) exposing an ion-sensitive field effect transistor (ISFET) to a protein phosphorylation reaction; and 2) detecting an electrical signal output from said ISFET.

Various embodiments can be used to identify a chemical reaction or to identify a compound that modulates a chemical reaction. For example, an embodiment of the invention may be utilized to evaluate the ability of a drug of interest to affect the phosphorylation rate on different substrates. This embodiment of the invention is useful for providing insight about drug specificity for certain biochemical pathways over others.

Still other embodiments are particularly useful in identifying and examining phosphorylation reactions.

The various embodiments of the methods of the present invention are capable of being carried out at low buffer concentrations.

In one aspect, the device of the present invention relates to an apparatus for detecting phosphorylation of an array of proteins, comprising: an array of sensors, each sensor comprising one ion-sensitive field effect transistor (ISFET); a layer of first material disposed over the sensor array and having formed therein a plurality of microwells, each microwell disposed over at least one of the ISFETs; each microwell comprising: a polypeptide comprising a test amino acid sequence and an affinity tag, a binding agent that recognizes the affinity tag and is attached to a surface of the microwell.

In another embodiment, the devices of the present invention include an ISFET which has a floating gate structure.

In yet another embodiment, the devices of the present invention can include a layer of protection material on the floating gate structure and wherein the protection material has a thickness of up to 600 Angstroms. For example, the protection material can be about 10-20 Angstroms, 20-100 Angstroms, 100-200 Angstroms, 200-300 Angstroms, 300-400 Angstroms, 400-500 Angstroms, 500-600 Angstroms, up to a total thickness of about 600 Angstroms.

In an embodiment of the invention, the ISFETs are CMOS devices, and the protection material comprises one or more layers of a CMOS passivation material.

BRIEF DESCRIPTION OF THE DRAWINGS

These and other features, aspects, and advantages of the present invention will become better understood with regard to the following description, appended claims, and accompanying drawings, in which:

DETAILED DESCRIPTION

The present invention is directed toward methods and devices based on combining ISFET chip construction architecture technology with that of protein array technology.

In a preferred embodiment, the present invention is directed toward methods and devices based on combining ISFET chip construction architecture technology with that of NAPPA technology for building protein arrays.

CMOS ISFET Devices and Methodology

Construction of the ISFET array chip architecture can be accomplished through various methods. In one embodiment of the invention, the ISFET array architecture disclosed by Rothberg et al. (U.S. 20100301398 A1 and Rothberg et al. 2011) can be utilized for the purposes of an aspect of the present invention. The methods and apparatuses disclosed by Rothberg et al. (US 20100301398 A1 and Rothberg et al. 2011) are incorporated herein by reference in their entirety for all purposes. Though developed specifically for DNA sequencing, the ISFET chip architecture and methodology disclosed by Rothberg et al. enables detection of any chemical reaction that produces protons as a reaction product.

Figure 1:
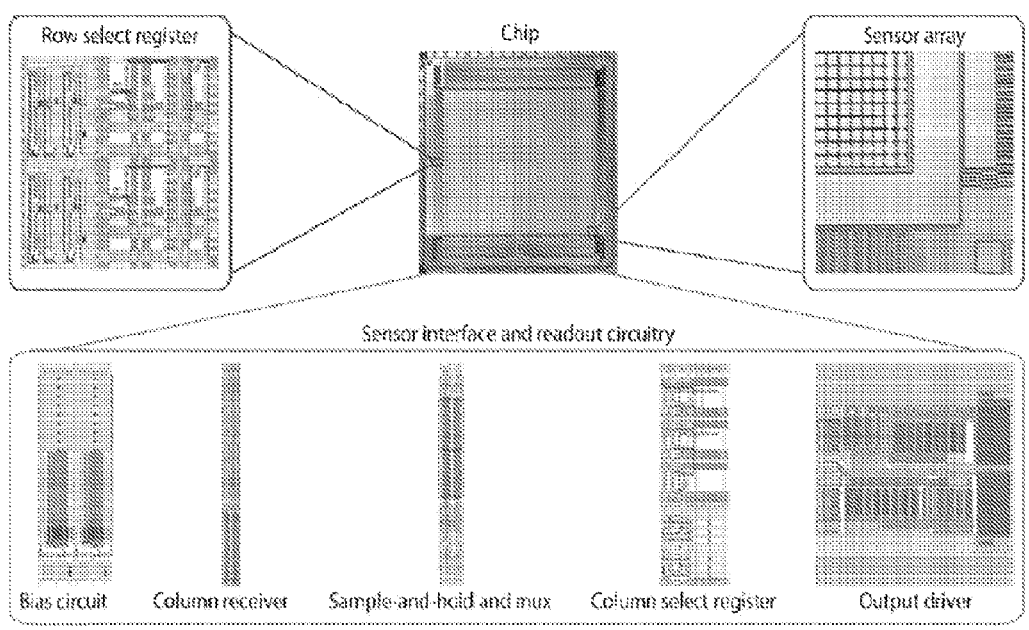
FIG. 1: shows functional blocks of the ion chip. Chip, with Row select registers, to sequentially address each row, and Sensor array, showing close up of the individual metal floating plates, Sensor interface and readout circuitry, containing Bias circuits, to set the operating current, Column receiver to set the operating voltage, Sample-and-hold and mux, to capture the output voltage, Column select register to sequentially address each column, and Output driver to transmit voltages off-chip for external data acquisition.

For example, Rothberg et al. teach the following ISFET chip architecture and methodology that may be utilized for purposes of the present invention:

A scalable ISFET sensor architecture using electronic addressing common in modern CMOS imagers (FIG. 1). An integrated circuit consisting of a large array of sensor elements, each with a single floating gate connected to an underlying ISFET (FIG. 2a). For sequence confinement, a 3.5-µm-diameter well formed by adding a 3-µm-thick dielectric layer over the electronics and etching to the sensor plate (FIG. 2b) is used. A tantalum oxide layer provides for proton sensitivity (58 mvpH$^{-1}$;

ref. 38). High-speed addressing and readout are accomplished by the semiconductor electronics integrated with the sensor array (FIG. 2c). The sensor and underlying electronics provide a direct transduction from the incorporation event to an electronic signal. Unlike light-based sequencing technology, the elements of the array do not collect photons and form a larger image to detect the incorporation of a base; instead each sensor is used to independently and directly monitor the hydrogen ions released during nucleotide incorporation.

Figure 3:
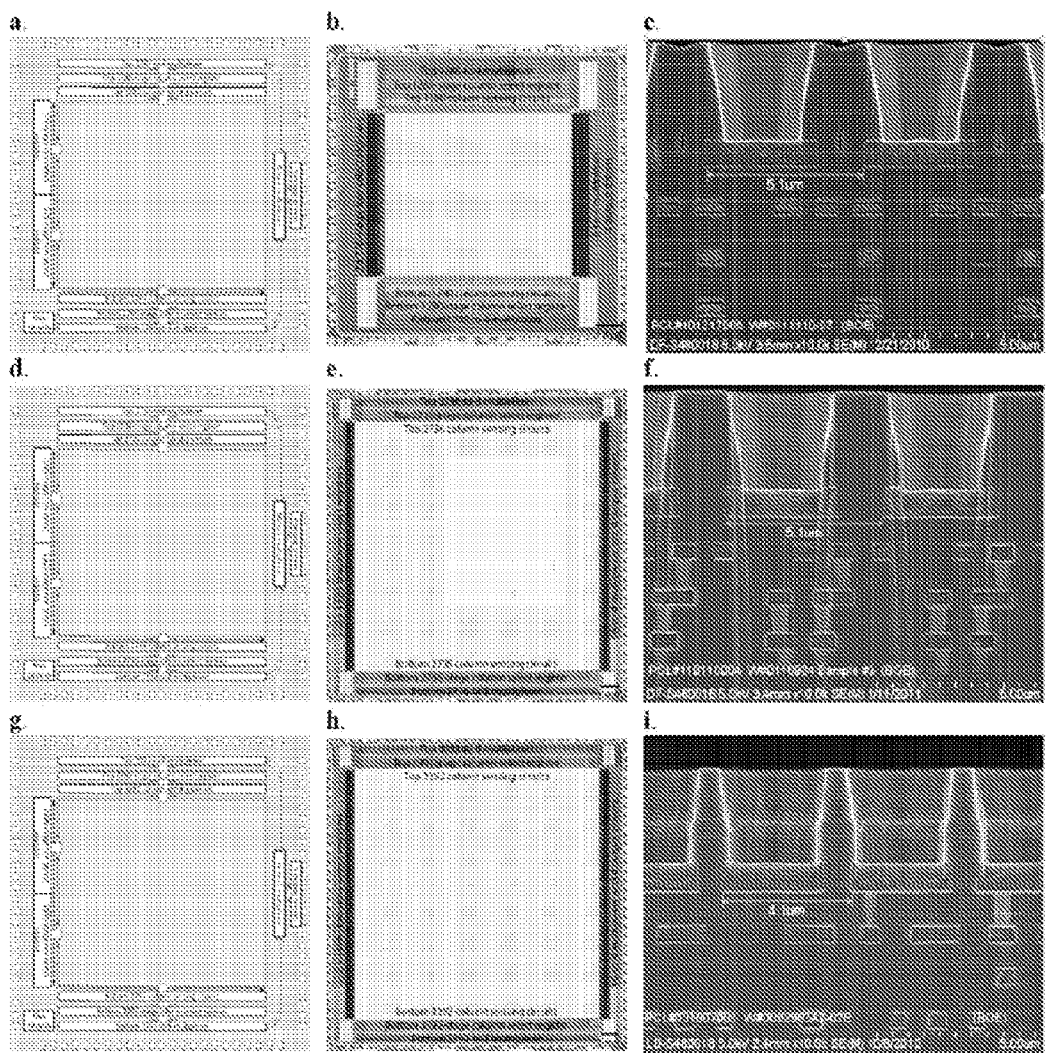
FIG. 3: shows three views of three ion chips: block diagram, photograph of single die, and scanning electron micrograph cross-sectional images of two adjacent wells aligned to the underlying electronic structure. a) is a chip with 1.5 M ISFETs has 1.2 M fluid-accessible sensors, b) measures 10.6 mm×10.9 mm, and c) has a 5.1 µm center-to-center pitch; d) is a chip with 7.2 M ISFETs has 6.1 M fluid-accessible sensors, e) measures 17.5 mm×17.5 mm, and f) has a 5.1 µm center-to-center pitch; g) is a chip with 13 M ISFETs has 11 M fluid-accessible sensors, h) measures 17.5 mm×17.5 mm, and i) has a 3.8 µm center-to-center pitch.

Ion chips are manufactured on wafers and cut into individual die. Chips can be designed and fabricated with 1.5 M, 7.2 M and 13 M ISFETs for example (FIG. 3).

Figure 2:
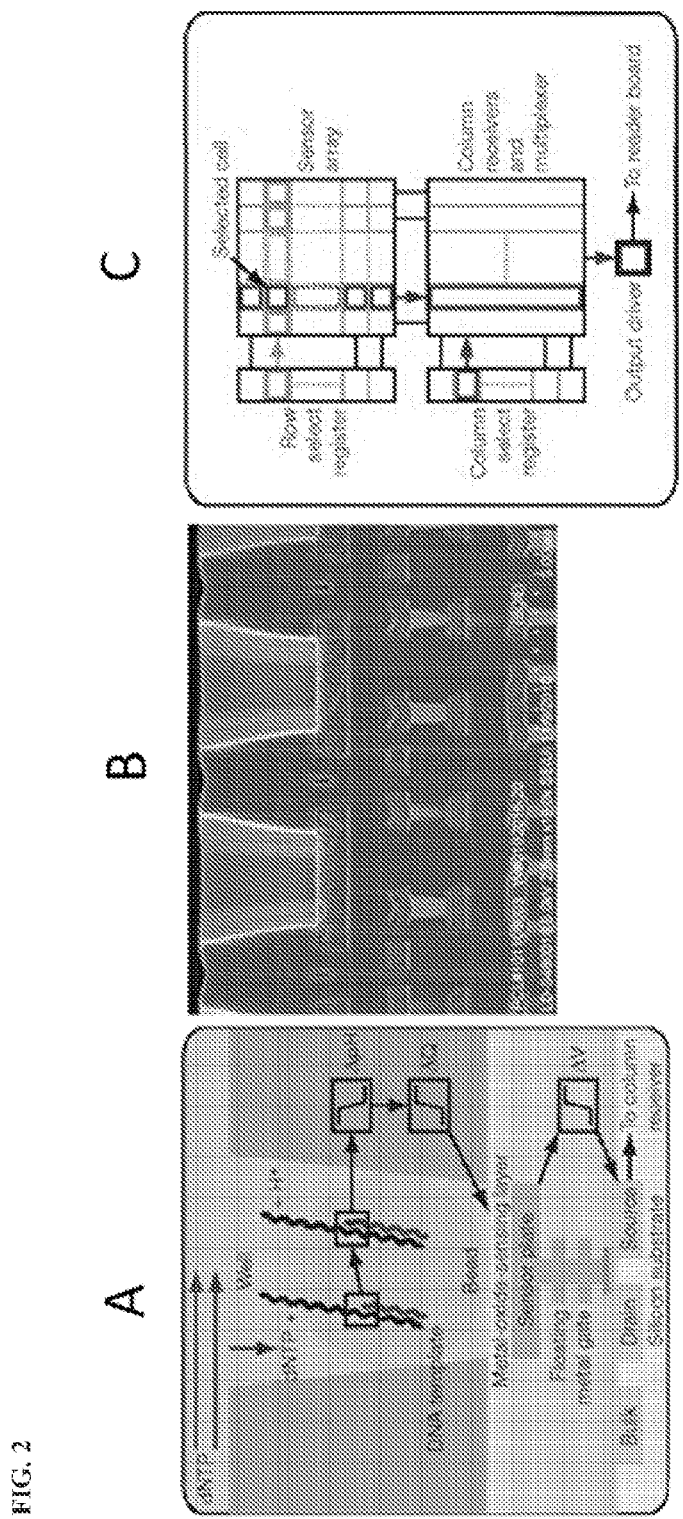
FIG. 2: shows a sensor, microwell, and chip architecture. A) illustrates a simplified drawing of a microwell, a bead containing DNA template, and the underlying sensor and electronics. Protons (H$^+$) are released when nucleotides (dNTP) are incorporated on the growing DNA strands, changing the pH of the well (ΔpH). This induces a change in surface potential of the metal-oxide-sensing layer, and a change in potential (ΔV) of the source terminal of the underlying field-effect transistor. B) is an electron micrograph showing alignment of the microwells over the ISFET metal sensor plate and the underlying electronic layers. C) is a schematic showing sensors arranged in a two-dimensional array. A row select register enables one row of sensors at a time, causing each sensor to drive its source voltage onto a column. A column select register selects one of the columns for output to external electronics.

In ion sequencing, all four nucleotides are provided in a stepwise fashion during an automated run. When the nucleotide in the flow is complementary to the template base directly downstream of the sequencing primer, the nucleotide is incorporated into the nascent strand by the bound polymerase. This increases the length of the sequencing primer by one base and results in the hydrolysis of the incoming nucleotide triphosphate, which causes the net liberation of a single proton for each nucleotide incorporated during that flow. The release of the proton produces a shift in the pH of the surrounding solution proportional to the number of nucleotides incorporated in the flow (0.02 pH units per single base incorporation). This is detected by the sensor on the bottom of each well, converted to a voltage and digitized by off-chip electronics. The signal generation and detection occurs over 4 s. After the flow of each nucleotide, a wash is used to ensure nucleotides do not remain in the well. The small size of the wells allows diffusion into and out of the well on the order of a one-tenth of a second and eliminates the need for enzymatic removal of reagents. (Quotation and Summarization of relevant sections of Rothberg et al., Nature 2011, Vol. 475, 348-352. FIGS. 1-3 also obtained from Rothberg et al.)

In one aspect of the present invention, the ISFET chip architecture described above in Rothberg et al. is utilized to construct a device for detecting phosphorylation of an array of proteins. The ISFET chip architecture comprising the component parts of the CMOS architecture described by Rothberg et al. is combined into a device that also utilizes NAPPA technology for creating polypeptide libraries across the surface of the array. In an embodiment, such polypeptides are contained within the microwells of the CMOS chip and each of the microwells are positioned directly over at least one ISFET.

Other ISFET chip architectures and methodologies are disclosed by Lee et al., in a recent review of the state of the art of ISFET technology. Lee et al. is herein incorporated by reference in its entirety for all purposes (Lee et al. 2009). These ISFET chip architectures and methodologies can be utilized in further embodiments of the present invention.

For example, Lee at al. teach the following ISFET chip architecture and methodology that may be utilized for purposes of the present invention:

When DNA strands bind to the gate surface of ISFETs, changes in surface potential occur due to the negative charge of DNA, thereby allowing for excellent performance in DNA sensing. Through special treatments of the oxide layer of a FET, probe DNA can be immobilized onto the oxide surface in an orientation-controlled manner. This allows a label-free detection of DNA using a FET device with a real-time electrical readout system for rapid, cost-effective, and simple analysis of DNA samples. (Quotation and Summarization of relevant sections of Lee et al.)

In another embodiment of the invention, the ISFET array architecture and methods disclosed by Goncalves et al. (Goncalves et al., 2008) can be utilized for the purposes of an aspect of the present invention. Goncalves et al. is hereby incorporated by reference in its entirety for all purposes. For Example, Goncalves et al. teach:

A detection platform based on an amorphous silicon-based (a-Si:H) ISFET for the label-free detection of covalent immobilization of DNA and subsequent hybridization of its complementary DNA. DNA binding behavior is monitored using an ISFET biosensor, and observed as changes in the threshold voltage (VTH). Through electric field monitoring, a sensitive response of a-Si:H ISFET to target DNA of different levels of hybridization is observed. (Quotation and Summarization of relevant sections of Goncalves et al., as explained in Lee et al.)

In still another embodiment of the invention, the ISFET array architecture and methods disclosed by Nebel et al. (Nebel et al., 2006) can be utilized for the purposes of an aspect of the present invention. Nebel et al. is herein incorporated by reference in its entirety for all purposes. For Example, Nebel et al. teach:

Detection of the hybridization of double stranded DNA using a single crystalline diamond synthesized by plasma-enhanced chemical vapor deposition (PECVD). To immobilize DNA onto the sensing layer of a constructed ISFET, amine linker-molecules can be covalently bound onto hydrogen-treated diamond surfaces by a photochemical method. Firstly, 3'-thiol-modified single stranded DNA is attached to the gate sensing layer of the diamond, and then the ssDNA-coated gate is hybridized with the complementary DNA. Gate potential shift was determined to be between 30 mV and 100 mV with the reduced DNA surface density using a DNA-ISFET device. In general, the variation in surface conductivity can be explained from the transfer doping model, in which the increase in hole density will cause a decrease of pH value in the surface conductive layer of the diamond. (Quotation and Summarization of relevant sections of Nebel et al., as explained in Lee et al.)

In another embodiment of the invention, the ISFET array architecture and methods disclosed by Estrela et al. (Estrela et al., 2005) can be utilized for the purposes of an aspect of the present invention. Estrela et al. is herein incorporated by reference in its entirety for all purposes. For Example, Estrela et al. teach:

MOS capacitors consisting of Au/SiO2/Si and Poly-Si TFTs with a gold metal gate as ISFET biosensor for label-free electrical detection of DNA hybridization. When probe DNA binds to its complementary DNA, changes in electric potential in the electric double layer occur, leading to a shift in the C-V (capacitance-voltage) or I-V (current-voltage) characteristics. By using this ISFET system with the appropriate DNA probes, it is potentially feasible to detect single-base-pair mismatches, revealing the possibility of the sensitive detection of single nucleotide polymorphisms (SNPs), one of the most frequent genetic alterations in the human population. (Quotation and Summarization of relevant sections of Estrela et al., as explained in Lee et al.)

In yet another embodiment of the invention, the ISFET array architecture and methods disclosed by Zayats et al. (Zayats et al., 2006) can be utilized for the purposes of an aspect of the present invention. Zayats et al. is herein incorporated by reference in its entirety for all purposes. For Example, Zayats et al. teach:

> The direct monitoring of adenosine as a target molecule. Upon the binding of adenosine to the cognate aptamer, changes in the electrical signal can be monitored with an ISFET. Following a primary silanization of Al2O3 gate with 3-aminopropyltriethoxysilane, the surface can be subsequently modified with glutaric dialdehyde. After the covalent immobilization of amine-functionalized aptamer on the gate surface, the hybridization of the nucleic acid to the aptamer can be investigated by ISFET measurement. Consequently, the tested ISFET-based aptamer sensor can exhibit the detection limit of approximately $5\times10^{-5}$ M, and will show high specificity, as the aptamer-modified ISFET will not respond to other nucleotides, such as cytidine. (Quotation and Summarization of relevant sections of Zayats et al., as explained in Lee et al.)

Nucleic Acid Programmable Protein Array Devices and Methodology

In an embodiment of the invention, ISFET array chip architecture is utilized as a platform upon which NAPPA technology is applied. One of the reaction products of kinase activity is a proton, making it detectable by an ISFET. Indeed, detection of kinase activity has been demonstrated for a single protein, though no mechanism was given. (Freeman et al., 2007). Thus, one embodiment of the present invention is a complimentary metal-oxide semiconductor (CMOS) chip that will allow assays of kinase activity across the entire proteome by combining the above disclosed ISFET chip architecture and methodology with NAPPA protein printing technology.

The NAPPA methods and devices disclosed by Ramachandran et al. (Ramachandran et al. 2004 and 2008) and LaBaer et al. (US 2005/0048580 A1) and LaBaer et al. (U.S. Pat. No. 6,800,453) can be utilized for the purposes of an aspect of the present invention. The teachings of these references are herein incorporated by reference in their entirety for all purposes.

Figure 4:
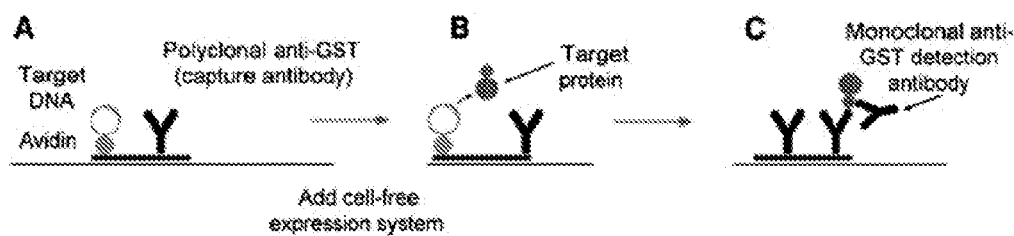
FIG. 4: illustrates a NAPPA approach. Biotinylation of DNA: Plasmid DNA is cross-linked to a psoralen-biotin conjugate with the use of ultraviolet light. A) Printing the array. Avidin (1.5 mg/ml, Cortex), polyclonal GST antibody (50 µg/ml, Amersham), and Bis(sulfosuccinimidyl) suberate (2 mM, Pierce) are added to the biotinylated plasmid DNA. Samples are arrayed onto glass slides treated with 2% 3-aminopropyltriethoxysilane (Pierce) and 2 mM dimethyl suberimidate. 2HCl (Pierce). B) In situ expression and immobilization. Microarrays are incubated with 100 µl per slide rabbit reticulocyte lysate with T7 polymerase (Promega) at 30° C. for 1.5 hours then 15° C. for 2 hours in a programmable chilling incubator (Torrey Pines). C) Detection. Target proteins are expressed with a C-terminal GST tag and immobilized by the polyclonal GST antibody. All target proteins can be detected using a monoclonal antibody to GST (Cell Signaling Technology) against the C-terminal tag confirming expression of full length protein.

For example, Ramachandran et al. teach the following NAPPA devices and methodology that may be utilized for purposes of the present invention:

> Building upon the successful use of in vitro translated protein in standard scale applications, the NAPPA approach substitutes the use of purified proteins with the use of cDNAs encoding the target proteins at each feature of a microarray. The proteins are transcribed and translated by a cell-free system and immobilized in situ by means of epitope tags fused to the proteins. This approach eliminates the need to express and purify proteins separately and produces proteins at the time of the assay, abrogating concerns about protein stability during storage. Mammalian proteins can be expressed in a mammalian milieu, providing access to vast collections of cloned cDNAs.
>
> A variety of cDNA printing schemes may be utilized in the NAPPA methodology. For instance, one may couple a psoralen-biotin conjugate to the expression plasmid DNA with the use of ultraviolet light, which is then captured on the surface by avidin (FIG. 4). Or, a printing chemistry that relies on the ability of bovine serum albumin (BSA) to dramatically improve DNA binding efficiency is also available for NAPPA. BSA and the capture antibody are coupled to an amine-coated glass surface via an activated ester-terminated homobifunctional crosslinker.
>
> The addition of a C-terminal glutathione S-transferase (GST) tag to each protein enables its capture to the array through an antibody to GST printed simultaneously with the expression plasmid. Other protein fusion tags and capture molecules can be easily substituted for GST in the NAPPA method.
>
> The key printed substrate for NAPPA is purified DNA, which is simpler to prepare, quantify, print and store than protein. High quality supercoiled DNA provides the best substrate for cell free protein expression, and commercial chemistries may provide insufficient yield and purity for this purpose. Therefore, the use of a resin derivatized with diamine chemistry, which enables the purification of high quality DNA efficiently, may be used in the NAPPA method.
>
> DNA binds the positively charged diamines at low pH and is eluted when they become neutrally charged under alkaline conditions. One technician can process 5000 samples/week with yields of 18 μg of supercoiled DNA per 1 ml of culture (5-10 fold greater than commercial systems). The DNA is of sufficient quality for use in mammalian cell transfections. (Quotation and Summarization of relevant sections of Ramachandran et al., Science 2004, Vol. 305, 86-90. FIG. 4 also obtained from Ramachandran et al.)

Another embodiment of the invention combines the CMOS ISFET chip architecture of Rothberg et al. and the NAPPA technology of Ramachandran et al. and LaBaer et al. into a methodology for monitoring a phosphorylation reaction. The U.S. Pat. No. 6,800,453, by LaBaer et al. and U.S. patent application Ser. No. 10/910,718, by LaBaer, are each hereby incorporated by reference in their entireties. The method comprises providing an array of ISFET sensors integrated into a CMOS chip architecture. The CMOS ISFET chip contains a plurality of microwells that are capable of holding solution. The microwells are positioned over at least one ISFET sensor, such that any ion fluctuations within the microwell may be detected by the transistors and perceived as a digital signal. In an embodiment, the microwells contain bound polypeptides. According to an embodiment, the polypeptides became bound within the microwells by utilization of NAPPA technology. Upon contacting the bound polypeptides with another polypeptide, a consequent change in ion concentration may be detected by the underlying ISFET sensors. The digital signal may further be analyzed, in an aspect of the methodology, by examining a computer read-out (graphical display) of the electrical signal. According to an aspect of the invention, such analysis of the detected digital signal will provide information pertinent to the kinetics of the detected phosphorylation reaction.

In still another method of the present invention, a technician would "query" the entire human proteome's susceptibility to kinase activity and or "query" the entire kinome.

Such an embodiment of the invention would entail utilizing the aforementioned ISFET CMOS chip architecture. A technician would "print" the entire proteome onto the ISFET chip utilizing NAPPA technology. The proteome on the chip would then be contacted by another analyte of interest, for example a kinase. The ISFET chip would detect within each microwell any resulting ion concentration change. Because each microwell contains a unique polypeptide printed onto its surface by NAPPA technology, it will be possible for a rapid analysis of the entire proteome's response to a given kinase.

Alternatively, another aspect of the invention concerns a methodology in which the entire kinome is queried. The procedure would be similar to the previous proteome analysis. The entire human kinome would be printed onto an ISFET CMOS chip utilizing NAPPA technology. The microwells of the chip would then be exposed to another analyte of interest and the resulting ion concentrations within each microwell would be detected by the transistor array. The procedure will allow a rapid analysis of the human kinome's response to a given analyte, for example a kinase inhibitor or promoter.

Figure 5:
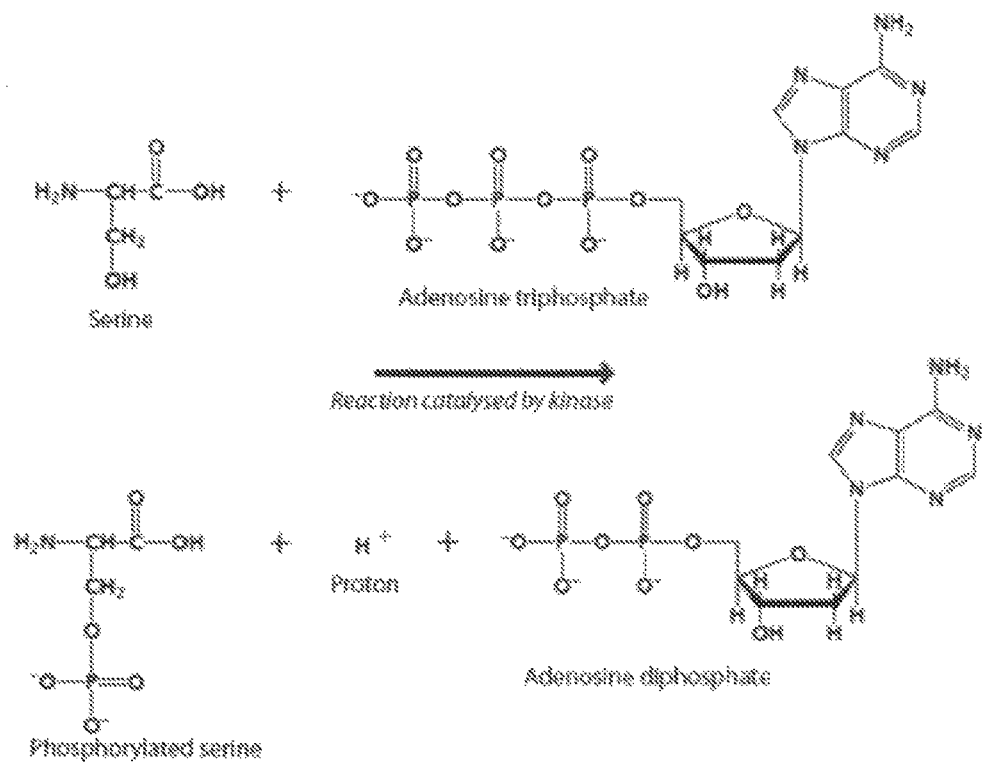
FIG. 5: shows a phosphorylation reaction of an isolated serine molecule, in which a proton is a reaction product.

Kinase Kinetics Via ISFET Measurement on a CMOS Chip Populated with a Protein Library Printed with NAPPA Technology In another embodiment of the invention, kinase kinetics can be examined via a combination of ISFET and NAPPA technology. Protein kinases are enzymes that modify neutral amino acid residues on target proteins to add a charged phosphate group. The action of a kinase is illustrated in FIG. 5 (where the target is shown as a single isolated and neutral serine—in practice it would be incorporated into a protein via amide bonds). Here, an exemplary reaction catalyzed by the kinase is the degradation of adenosinetriphosphate into adenosinediphosphate, and the replacement of the H in the hydroxyl group of the serine residue with a charged phosphate. A proton is released in the reaction, so an ISFET can be used to monitor the course of the reaction. In order to exploit the potential parallelism of Very-large-scale integration (VLSI), NAPPA is utilized to reliably print the entire human proteome onto a chip, one colony of identical proteins above each ISFET. If this were done, then it would be possible to address the entire proteome to ask which proteins were phophorylated by a given kinase, and then to ask how various drugs affect the rate of particular kinase-protein interactions.

In another embodiment of the invention, Nucleic Acid Programmable Protein Arrays (NAPPA) are produced by printing the genes for each protein onto a chip. Each gene is modified to contain the code for trapping of the protein product by a capture element that is also programmed onto the array. The double stranded DNA is stable indefinitely. When a protein chip is required, the chip is flooded with cell extract. The genes are transcribed into RNA and the RNA translated into proteins by ribosomes in the cell extract. Each protein is confined to the well in which its gene was printed, because of the capture reagent coded into it. Building protein arrays on top of ISFET arrays enables massively parallel assays of kinase activity and inhibition.

Figure 6:
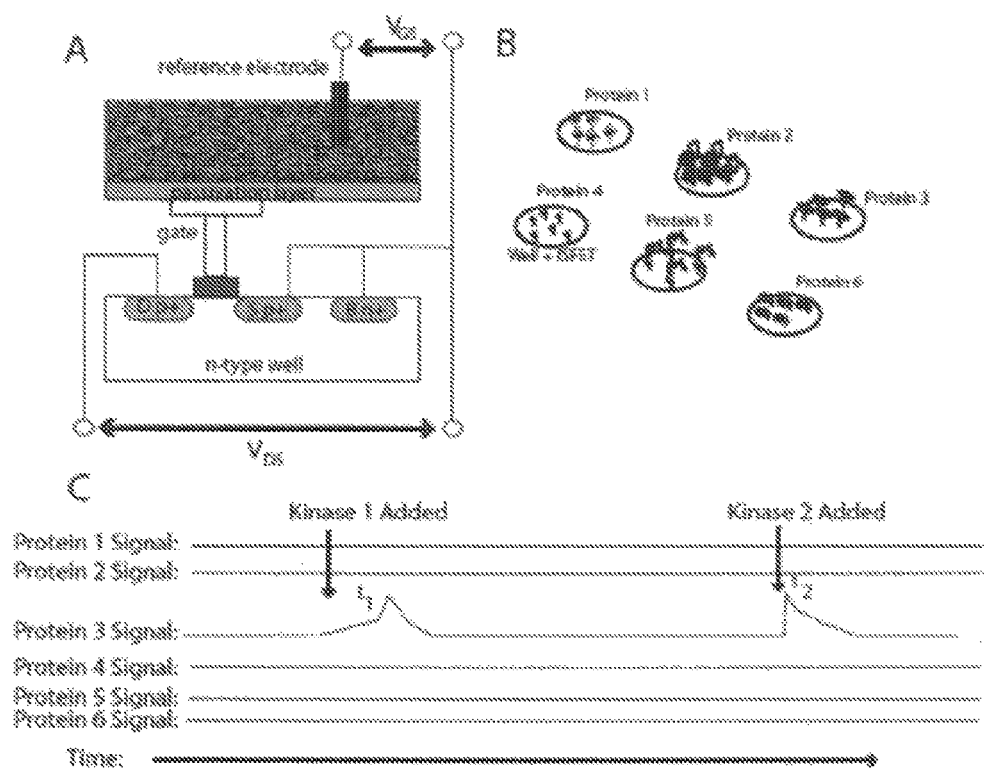
FIG. 6: shows a device for electronic detection of kinase activity on a protein array. A) shows a single ISFET schematically. B) shows an array of proteins printed by NAPPA technology—each microwell sits over the gate of an individual ISFET and has multiple copies of one type of protein. C) shows how the signal from the ISFET identifies which proteins are kinase targets and how the kinetics of phosphorylation can be quantified.

In an embodiment of the invention, an ISFET device is constructed as represented generally by the schematic in FIG. 6. FIG. 6A shows the construction of an ISFET as is known in the art and constructed by references to the literature previously cited. The gate is controlled by charge on a silicon dioxide layer, for example, that covers it and this is pH sensitive owing to the competing reactions with silanol groups on the surface:

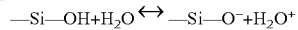

An array of ISFETs is arranged with microwells above the gate electrode (which may be a floating gate in some embodiments) the lower surface of the well forming the glass dielectric that covers the gate. A different polypeptide is grown in each well using the NAPPA technology (See FIG. 6B).

Kinase targets can be identified from the ISFET signal generated when the local pH is changed. FIG. 6C shows what an appropriate ISFET signal would look like according to an aspect of the invention. In the hypothetical example, protein 3, and only protein 3 in this case, is a target of kinase 1 and 2, the two kinases having been flushed over the chip with a rinse in between.

The kinetics of the phosphorylation reaction are obtained from the shape of the waveform of the ISFET signal as a function of time. In the hypothetical example shown, kinase 1 acts more slowly than kinase 2 (ti>t2). The kinetics of kinases can be readily understood by those of skill in the art based upon signals that will be presented according to the invention.

Experiment 1: Kinase Activity in Low Buffer Concentration

In some embodiments, it can be important for ISFET detection that reactions take place in conditions of low buffer concentration, in order that the local change of pH detected by the ISFET is maximized. Concentrations of buffer may be: 300-200 mM, 200-100 mM, 100 mM-50 mM, 50-40 mM, 40-30 mM, 30-20 mM, 20-10 mM, 10-5 mM, 5 mM-0 mM. We show here that kinase activity is maintained in low buffer concentration. Thus, with a combination of NAPPA technology and an ISFET array, proteome-wide assays of kinase kinetics become possible. This makes available a very simple assay for finding kinase targets and for quantifying the activity of drugs that act as kinase inhibitors.

Strong buffers will tend to mask the pH spike produced by the kinase activity and it is generally believed that buffering is required for kinase activity, because a lowering of pH increases the free energy of the reaction products.

Figure 7:
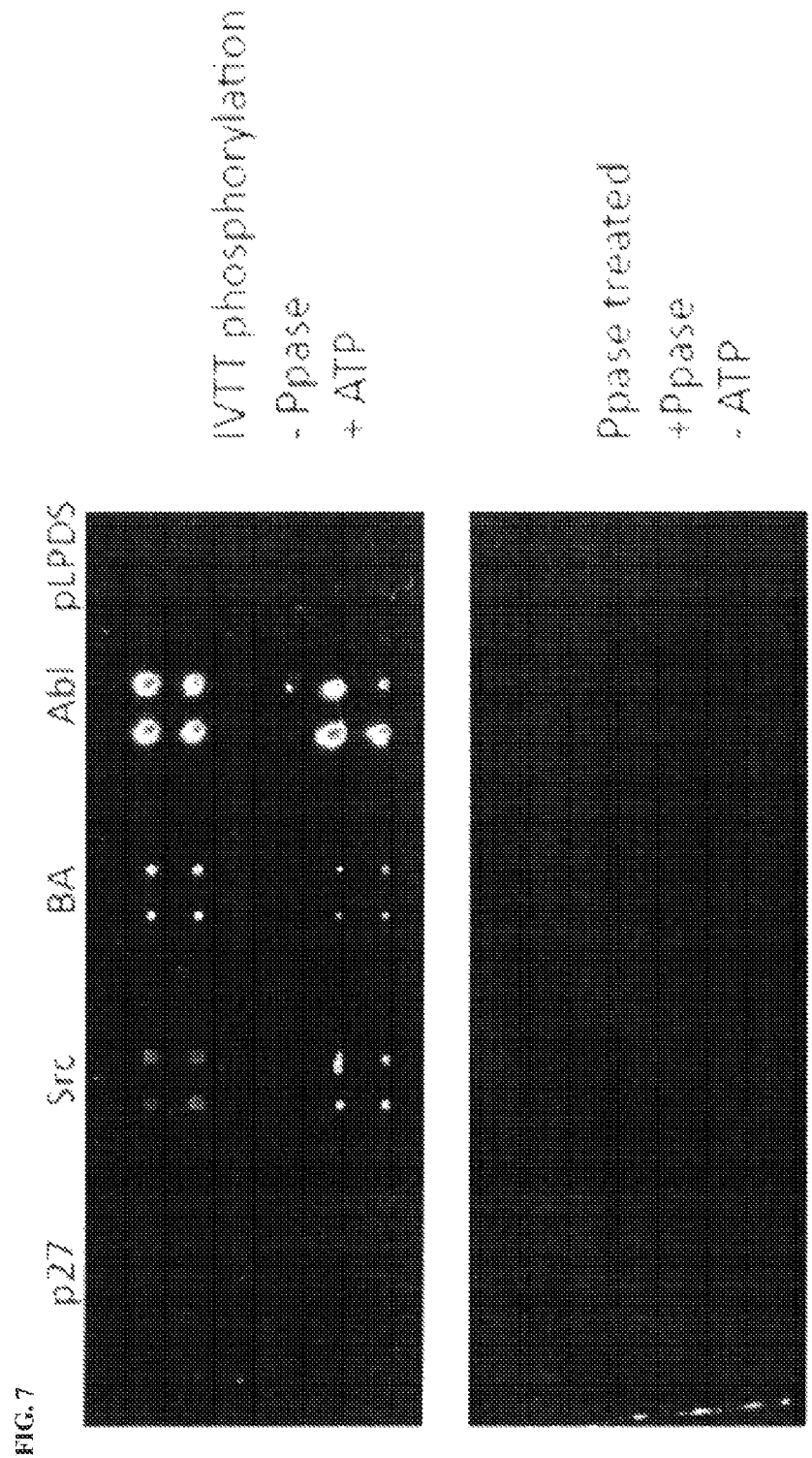
FIG. 7: shows an array used for testing kinase activity in different buffers. The array contains five different proteins (each duplicated as 8 spots, grouped in two sets of four spots). Three of the proteins were kinases that autophosphorylate themselves in the presence of ATP (Src, BA and Abl). Two controls were added at each end of the array: p27 (left end) and pLPDS (right end). New phosphorylation was confirmed as the source of signal, because any previous phosphorylation was removed when the array was first treated with phosphatase, as illustrated by the bottom image.
Figure 8:
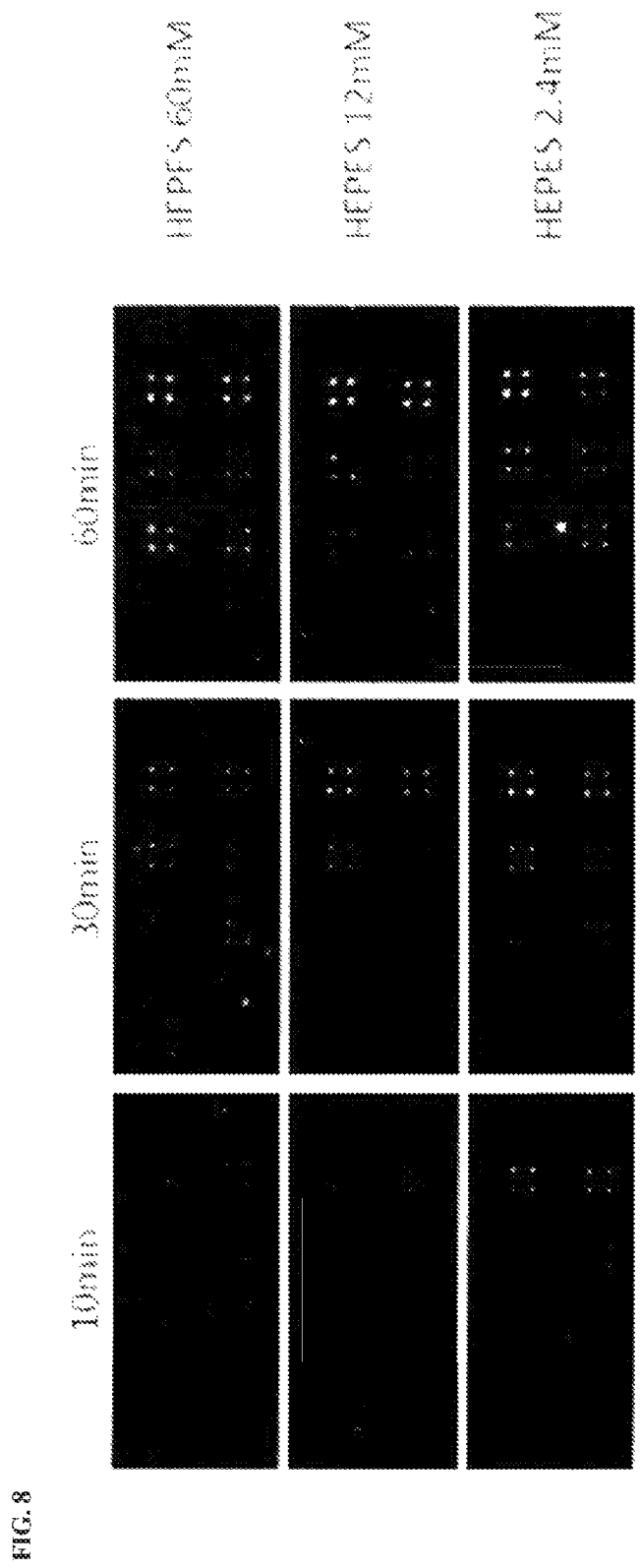
FIG. 8: shows an array used for testing kinase activity in HEPES buffer down to a concentration of 2.4 mM. The array contains the same variety of five proteins as in FIG. 7 (each duplicated as 8 spots, grouped in two sets of four spots). Three of the proteins were kinases that autophosphorylate themselves in the presence of ATP (Src, BA and Abl). Two controls were added at each end of the array: p27 (left end) and pLPDS (right end), as identified in FIG. 7.

In order to test different buffers, an array of 5 different proteins is printed (each duplicated as 8 spots, grouped in two sets of four spots). Three of the proteins were kinases that autophosphorylate themselves in the presence of ATP (Src, BA and Abl). Two controls were added at each end of the array: p27 (left end of FIG. 7) and pLPDS (right end of FIG. 7). These controls are proteins that lack kinase activity. The array was first treated with phophotase to ensure that no phosphorylation was present at the start of the experiment. The array was then exposed to ATP in standard conditions (25 mM Tris-HCL (pH 7.5), 5 mM beta-glycerophosphate, 2 mM DTT, 0.1 mM Na3VO4, 10 mM MgCl2, 400 uM ATP) for 60 min and then incubated with a fluorescently-labeled antibody to phosphorylated tyrosine. The top panel showed clearly that, in the absence of phophotase, the three proteins with kinase activity autophosphorylate. With reduction of Tris buffer concentration below these standard conditions, it was found that kinase activity was reduced. However, when the experiment was repeated with HEPES buffer (standard conditions are 60 mM HEPES-NaOH (pH 7.5), 2.5 mM DTT, 3 uM Na3VO4, 5 mM MgCl2, 400 uM ATP) it was found that the HEPES concentration could be dropped all the way down to 2.4 mM with no impact on the reaction (FIG. 8, the times listed are times of incubation with ATP). Thus, it was discovered the surprising ability to utilize low buffer conditions in the phosphorylation reactions that will be valuable in creating sensitive ISFET CMOS detection systems.

Figure 9:
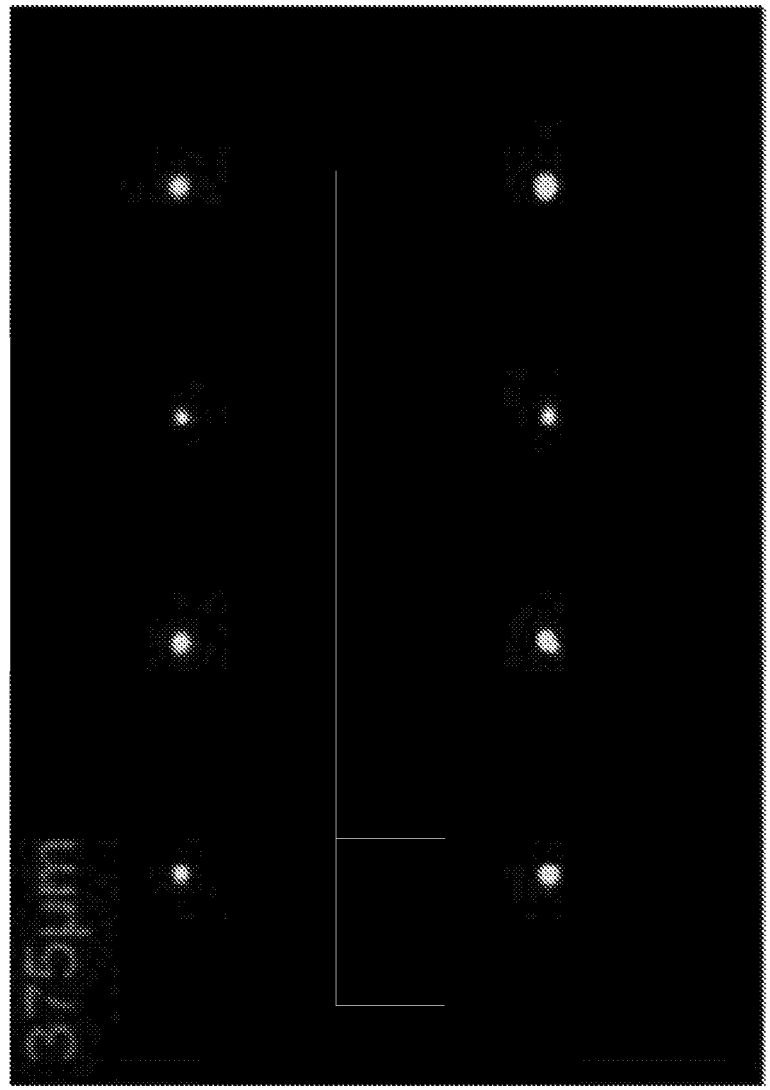
FIG. 9: shows a plate of 70 genes, cloned with a Halo tag at the c-terminus of the protein, were prepared by DNA miniprep, printed, expressed, and the resulting proteins captured to the surface through covalent attachment of the Halo protein to a chloroalkane compound coating the surface. The printed proteins were probed with an anti-p53 mAb in duplicate (top half and bottom half of FIG. 9). p53 was included in the plate four times thus displaying eight p53 features total. The highly specific anti-p53 signal was displayed with anti-mouse IgG labeled with fluorescent dye.

Experiment 2: NAPPA Chemistry Utilizing Halo Coupling to Minimize Distance of Protein From ISFET Gate In order to minimize the distance between a bound protein and an ISFET gate, experiments were performed verifying the viability of utilizing Halo tag binding chemistry in NAPPA. A plate of 70 genes, cloned with a Halo tag at the c-terminus of the protein, were prepared by DNA miniprep, printed, expressed, and the resulting proteins captured to the surface through covalent attachment of the Halo protein to a chloroalkane compound coating the surface. The printed proteins were probed with an anti-p53 mAb in duplicate (top half and bottom half of FIG. 9). p53 was included in the plate four times thus displaying eight p53 features total. The highly specific anti-p53 signal was displayed with anti-mouse IgG labeled with fluorescent dye.

By demonstrating the functionality of Halo tag binding chemistry, another binding chemistry suitable for use in ISFET CMOS devices has been illustrated. This new binding chemistry alleviates any concern that the phosphorylation reactions may be too far above the surface of the ISFET to be detected. Halo is a 24 kD protein tag that is essentially a suicide enzyme. When it encounters a chloroalkane compound it forms a covalent bond to it. Thus, a CMOS surface could be coated with chloroalkane and then the protein will bind thereto.

Experiment 3: Detection of Phosphorylation on an ISFET Device Utilizing NAPPA Methodology to Print the Protein Onto the ISFET Device The viability of utilizing the NAPPA methodology to print a protein onto an ISFET device was examined. Two experiments were conducted to test the technology. The results from the first experiment are explained below.

The auto-phosphorylating protein Src was printed onto an ISFET device utilizing the NAPPA method. In the presence of ATP, Src phosphorylates itself, releasing a $H^+$ ion. The $H^+$ ion released is then detectable by the ISFET device.

Figure 10:
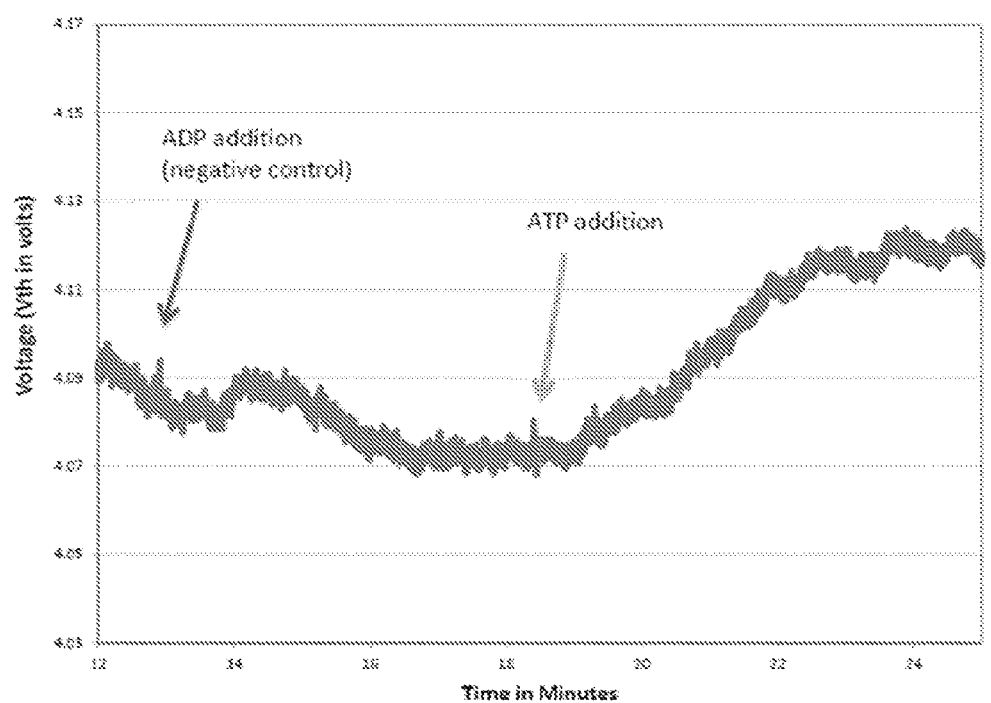
FIG. 10: shows an ISFET device detection of phosphorylation of a protein printed to the ISFET device utilizing NAPPA methodology. The protein utilized was auto-phosphorylating protein SRC. ADP was the negative control.

Subsequent to expression of the Src protein on the ISFET device, ATP was introduced onto the device. As can be seen from FIG. 10, once ATP was added to the ISFET device there was a corresponding and detectable upward shift in the threshold voltage measured by the device.

Furthermore, ADP was introduced to the device, in order to provide a negative control treatment. As can be seen from FIG. 10, ADP introduction did not cause a corresponding upward threshold voltage shift in the device.

The experiment demonstrates the utility of utilizing ISFET architecture in conjunction with the NAPPA methodology to provide an accurate and highly multiplexable platform for measuring phosphorylation kinetics.

Experiment 4: Detection of Phosphorylation on an ISFET Device Utilizing NAPPA Methodology to Print the Protein Onto the ISFET Device The viability of utilizing the NAPPA methodology to print a protein onto an ISFET device was examined. Two experiments were conducted to test the technology. The results from the second experiment are explained below.

The auto-phosphorylating protein Src was printed onto an ISFET device utilizing the NAPPA method. In the presence of ATP, Src phosphorylates itself, releasing a $H^+$ ion. The $H^+$ ion released is then detectable by the ISFET device.

Figure 11:
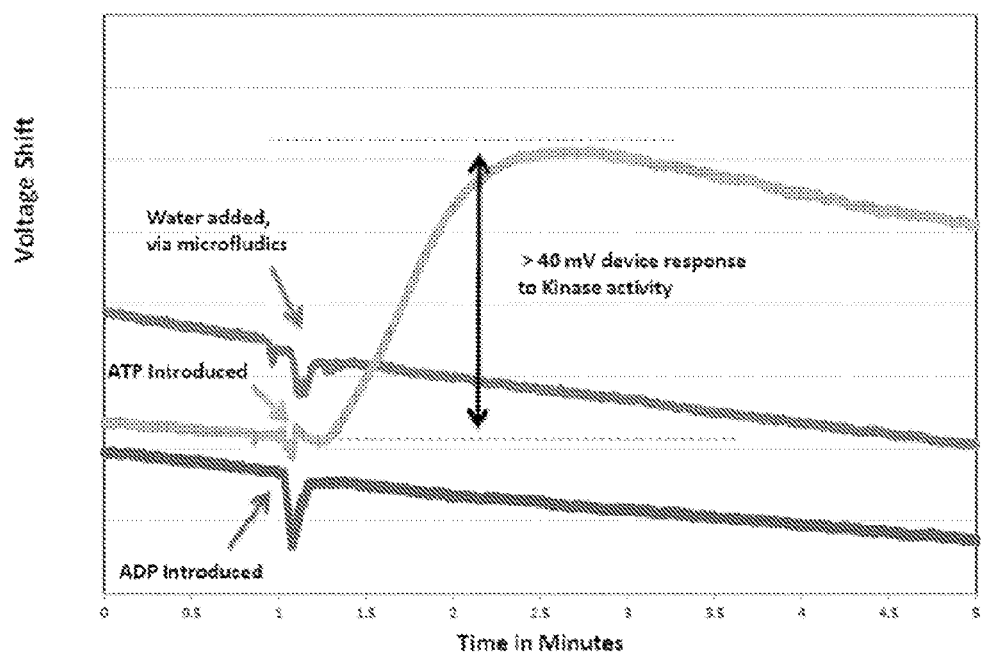
FIG. 11: shows all ISFET device detection of phosphorylation of a protein printed to the ISFET device utilizing NAPPA methodology. The protein utilized was auto-phosphorylating protein SRC. ADP and water were the negative controls.

Subsequent to expression of the Src protein on the ISFET device, ATP was introduced onto the device. As can be seen from FIG. 11, once ATP was added to the ISFET device there was a corresponding and detectable upward shift in the threshold voltage measured by the device.

Furthermore, water and ADP were introduced to the device, in order to provide two negative control treatments. As can be seen from FIG. 11, neither water nor ADP introduction caused a corresponding upward threshold voltage shift in the device.

The experiment further demonstrates the utility of utilizing ISFET architecture in conjunction with the NAPPA methodology to provide an accurate and highly multiplexable platform for measuring phosphorylation kinetics.

REFERENCES CITED

Manning et al., "The Protein Kinase Complement of the Human Genome," Science, 2002, Vol. 298, No. 5600, 1912-1934.

NIH Primer on Microarrays. (http://www.ncbi.nlm.nih.gov/About/primer/microarrays.html)

Lee et al., "Ion-Sensitive Field-Effect Transistor For Biological Sensing," Sensors, 2009, Vol. 9, 7111-7131.

Ramachandran et al., "Self-Assembling Protein Microarrays," Science, 2004, Vol. 305, 86-90.

Ramachandran et al., "Next Generation High Density Self Assembling Functional Protein Arrays," Natural Methods, 2008, June, 5(6), 535-538.

Rothberg et al., "An Integrated Semiconductor Device Enabling Non-Optical Genome Sequencing," Nature, 2011, Vol. 475, 348-352.

Rothberg et al., "Methods and Apparatus for Measuring Analytes," US Patent Publication Number (US 20100301398 A1), U.S. patent application Ser. No. 12/475,311.

Goncalves et al., "Detection of DNA and Proteins Using Amorphous Silicon Ion-Sensitive Thin-film Field Effect Transistors," Biosens. Biolectron., 2008, Vol. 24, 545-551.

Nebel et al., "Alkene/Diamond Liquid/Solid Interface Characterization Using Internal Photoemission Spectroscopy," Langmuir, 2006, Vol. 22, 5645-5653.

Estrela et al., "Field Effect Detection of Biomolecular Interactions," Electrochim. Acta, 2005, Vol. 50, 4995-5000.

Zayats et al., "Label-free and Reagentless Aptamer-Based Sensors for Small Molecules," J. Am. Chem. Soc., 2006, Vol. 128, 13666-13667.

LaBaer et al., "Nucleic-Acid Programmable Protein Arrays," US Patent Publication Number (US 20050048580 A1), U.S. patent application Ser. No. 10/910,718.

LaBaer et al., "Nucleic-Acid Programmable Protein Arrays," (U.S. Pat. No. 6,800,453).

Freeman et al., "Following a Protein Kinase Activity Using a Field-Effect Transistor Device," Chem. Commun., 2007, Vol. 33, 3450-3452.

What is claimed is:

1. A method for evaluating phosphorylation of an array of proteins, comprising:
    1) exposing an ion-sensitive field effect transistor (ISFET) to a protein phosphorylation reaction; and
    2) detecting an electrical signal output from said ISFET;
        wherein the ISFET is integrated into a complementary metal-oxide semiconductor (CMOS);
        wherein a CMOS surface is coated with a chloroalkane compound; and
        wherein at least one protein comprising a protein tag involved in the protein phosphorylation reaction is deposited onto the CMOS surface by using nucleic-acid programmable protein array (NAPPA) technology.

2. The method of claim 1, wherein the phosphorylation reaction takes places under buffer concentrations below 5.0 mM.

3. The method of claim 1, further comprising the step of analyzing the detected electrical signal to discriminate discrete fluctuations in the electrical signal, wherein the electrical signal indicates a change in H+ or OH− ion concentration.

4. The method of claim 3, further comprising the step of determining the kinetics of the phosphorylation reaction by evaluating the waveform of the electrical signal output.

5. The method of claim 1, wherein the protein tag is a hydrolase protein tag.

* * * * *